United States Patent [19]

Nokihara et al.

[11] Patent Number: 5,234,836
[45] Date of Patent: Aug. 10, 1993

[54] METHOD FOR AMINO ACID SEQUENCE ANALYSIS

[75] Inventors: Kiyoshi Nokihara, Uji; Koji Muramoto, Iwate, both of Japan

[73] Assignee: Shimadzu Corporation, Kyoto, Japan

[21] Appl. No.: 841,797

[22] Filed: Feb. 26, 1992

[30] Foreign Application Priority Data

Feb. 28, 1991 [JP] Japan .................. 3-059740

[51] Int. Cl.⁵ .......................... G01N 33/68
[52] U.S. Cl. ........................ 436/89; 436/161; 436/172
[58] Field of Search .................. 436/89, 161, 172

[56] References Cited

U.S. PATENT DOCUMENTS 4,865,994  9/1989  Tsugita et al. .............. 436/89 X

FOREIGN PATENT DOCUMENTS 0244055  11/1987  European Pat. Off. .
0353361  2/1990  European Pat. Off. .

OTHER PUBLICATIONS

Kent, S., et al, "Approaches to Sub-Picomole Protein Sequencing", vol. 5, No. 4, (1987), *BioTechniques*, pp. 314–320.

Database WPIL, week 8648, Derwent Publications, Ltd., London, GB; AN 86-315348 & JP-A-61 233371 (Toyo Soda Mfg KK) 17 Oct. 1986.

Database WPIL, Week 8642, Derwent Publications, Ltd., London GB; AN 86-275161 & JP-A-61 199983 (Fuji Photo Film KK) 4 Sep. 1986.

*Primary Examiner*—Jill A. Johnston
*Attorney, Agent, or Firm*—Oblon, Spivak, McClelland, Maier & Neustadt

[57] ABSTRACT

The present invention is directed to a method for amino acid sequence analysis comprising either the steps of labeling the sample with a fluorescent reagent and quenching the excess fluorescent reagent remaining after said labeling with an ammonium salt, or the steps of degrading amino acid from the amino terminus of peptides or proteins using a fluorescent Edman reagent and quenching the excess fluorescent Edman reagent remaining after said degrading with an ammonium salt. The method of the present invention makes it possible to eliminate the interference of identification by the chromatographic peak of fluorescent reagent by quenching the excess fluorescent reagent in the sample.

8 Claims, 7 Drawing Sheets

METHOD FOR AMINO ACID SEQUENCE ANALYSIS

FIELD OF THE INVENTION

The present invention relates to a method for amino acid sequence analysis. More specifically, the invention relates to a method for microsequencing of peptides or proteins using a fluorescent reagent wherein the excess fluorescent reagent is quenched before ultrahigh-sensitive liquid chromatography for the identification of the released amino acid derivative. This invention can be extended to the fluorescent labeling using any fluorescent reagents of any amino compound such as amino sugars, amino acids, peptides, proteins, and so on.

BACKGROUND OF THE INVENTION

Traditionally, in analysis of the primary structure of proteins and others, the Edman method has been used, in which a labeled amino acid such as 3-phenyl-2-thiohydantoin (PTH)amino acid is assayed by reverse phase high performance liquid chromatography. However, since this method is based on UV absorption, it is significantly affected by background factors such as the organic solvent of the eluent and decomposition products, and the sensitivity is insufficient.

In recent years, a microassay method based on fluorescence has been developed to meet the requirements for quicker analysis and higher precision. In this method, the amino group in amino acid is labeled with a fluorescent reagent, including an isothiocyanate derivative such as fluorescein isothiocyanate (FITC).

Usually, it is necessary to eliminate the excess reagent after labeling the fluorescent reagent; a problem has been pointed out that it is difficult to set conditions for elimination of the excess reagent in the case of FITC and other reagents having a hydrophilic functional group in their molecular structure.

When the compound to be detected is a compound whose polarity is different from that of the isothiocyanate derivative, the reaction solution may be isolated directly by chromatography after labeling with the fluorescent reagent. On the other hand, in the case of compounds having a hydrophilic functional group, such as amino acids and sugars, it is often difficult to separate the labeled derivative from the excess reagent. If this excess fluorescent reagent remains in the sample, a problem arises that the identification of amino acid derivatives is hampered in the detection of amino acids such as tryptophan and amino sugars such as glucosamine and galactosamine because the chromatographic peaks overlap or appear very closely.

On the other hand, if the excess reagent is completely washed out, the target amino acids etc. in the sample are flown out, which results in reduction in the sample volume.

SUMMARY OF THE INVENTION

It is an object of the present invention to provide a method for amino acid sequence analysis using a fluorescent reagent wherein the interference on amino acid identification by chromatographic peaks is eliminated by quenching the excess fluorescent reagent which exists after labeling the sample or stepwise degradation of peptides or proteins.

With the aim of solving the problems described above, the present inventors made investigations to eliminate the interference of the excess fluorescent reagent remaining after labeling or stepwise degradation of peptides or proteins, and developed the invention.

Accordingly, the object of the present invention essentially relates to a method for amino acid sequence analysis having a process in which the excess fluorescent reagent remaining after labeling the sample with the fluorescent reagent, or stepwise degradation of peptides or proteins with the fluorescent Edman reagent is quenched by reacting said excess fluorescent reagent with an ammonium salt.

According to the method of the present invention, the remaining excess fluorescent reagent alone is reacted without influence on the labeled compound by adding an ammonium salt, and the resulting compound does not affect the detection of the target compound.

DETAILED DESCRIPTION OF THE INVENTION

Figure 1:
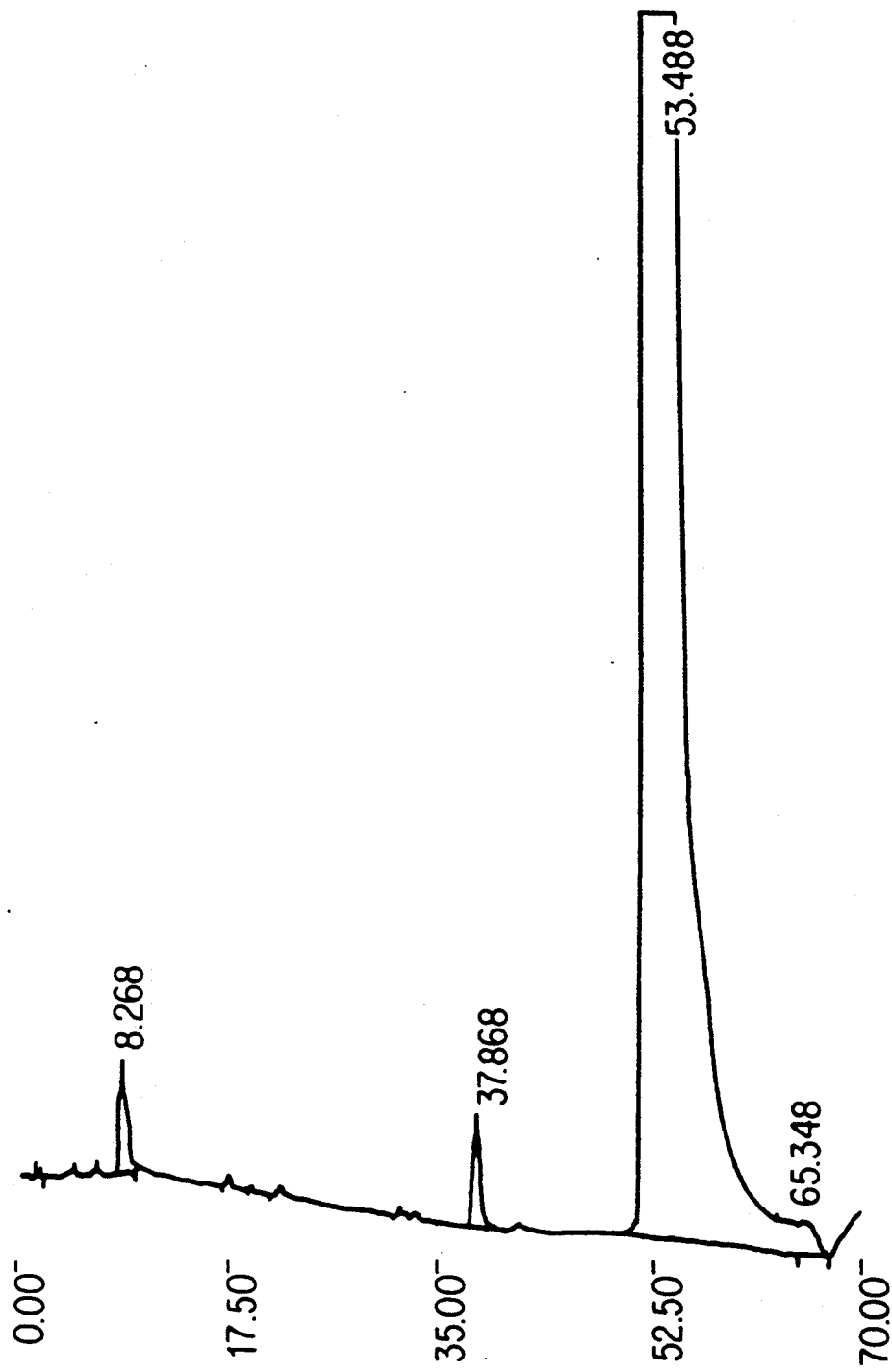
FIG. 1 shows the HPLC chart for FITC-I alone in the absence of ammonium acetate.

Examples of the fluorescent reagent for the present invention include known fluorescent reagents such as fluorescein isothiocyanate (FITC). FITC, having reactivity with amino group, can be converted to aminofluorescein, a precursor for synthesis of FITC, by reaction with ammonium salt. The polarity of the aminofluorescein produced by this conversion is much higher than that of FITC, and its fluorescence intensity is about 50%.

In addition to FITC descrived above, examples of the fluorescent reagent for the present invention include 4-(N-1-dimethylaminonaphthalene-5-sulfonylamino) phenylisothiocyanate, any of which can be used for the present invention.

Examples of the ammonium salt for the present invention include organic ammonium salts such as ammonium acetate. Any of these ammonium salts may be used, as long as it has no effect on the target compound in the sample, and may be used singly or in combination of two or more kinds.

Usually, in amino acid sequence analysis using a fluorescent reagent, an excess reagent is present in the sample because the fluorescent reagent is used in much excess relative to the target compound. Ammonium salt is used at concentrations of not less than 0.1 mol, preferably about 100 to 1000 mol per mol of the excess reagent.

In the method for quenching the excess fluorescent reagent according to the present invention, ammonium salt is added and reacted with the excess fluorescent reagent in the sample as stated above, but in this case it is usually preferable to heat to about 55° C. from the viewpoint of reactivity. Usually, a reaction time of about 10 minutes is sufficient.

The aminofluorescein produced from excess FITC by such a treatment does not affect the assay of the target compound even when it is present in the sample, and its fluorescence intensity is half that of FITC; therefore, it is unnecessary to eliminate it from the sample.

The apparatus for amino acid sequence analysis of the present invention is equipped with a means for quenching the excess fluorescent reagent remaining after labeling or stepwise degradation of peptides or proteins. This means for quenching is achieved by additing and reacting an ammonium salt as described above. In the apparatus for amino acid sequence analysis, the addition of an ammonium salt is conducted by preparing it in one of the reaction reagent bottles and adding the predetermined amount of it to reaction vessel. In the present invention, as stated above amino acid sequence analysis is carried out at least by the following steps of labeling a sample with a fluorescent reagent and quenching the excess fluorescent reagent remaining after said labeling with an ammonium salt, and when the fluorescent reagent is used as a Edman reagent, the steps are degrading amino acid from the amino terminus of peptides or proteins using a fluorescent Edman reagent and quenching the excess fluorescent Edman reagent remaining after said degrading with an ammonium salt.

The method of the present invention makes it possible to eliminate the interference of identification by the chromatographic peak of fluorescent reagent, for example FITC, by quenching the excess fluorescent reagent in the sample. Therefore, microassay of amino acids including tryptophan and amino sugars including glucosamine, galactosamine and mannosamine is possible.

This method is also applicable to fluorescence protein sequencers, amino acid microassay, amino sugar microassay and other assays.

EXAMPLES

The present invention is hereinafter described in more detail by means of the following examples, but the invention is not limited thereby.

EXAMPLE 1

FITC-I (20 nmol/100 μl) was dissolved in acetonitrile-0.1 M ammonium acetate (pH 9.0) (9:1) and heated to 55° C. After 0 minute (immediately after dissolution, not heated), 5 minutes and 10 minutes of heating, 1 μl (200 pmol) was subjected to high performance liquid chromatography (HPLC).

The conditions for HPLC used were: column: Hypersil ODS (2 columns, 3 μm, 4.6×100 mm, 4.6×50 mm); temperature: 60° C.; flow rate: 1.0 ml/min; solvent A: 3% acetone-10 mM phosphate buffer (PB) (pH 7.0); solvent B: 15% acetone-10 mM PB (pH 7.0); gradient: Solvent B(%), 0 minute: 0%; 30 minutes: 50%; 45 minutes: 50%; 60 minutes: 100%.

Figure 2:
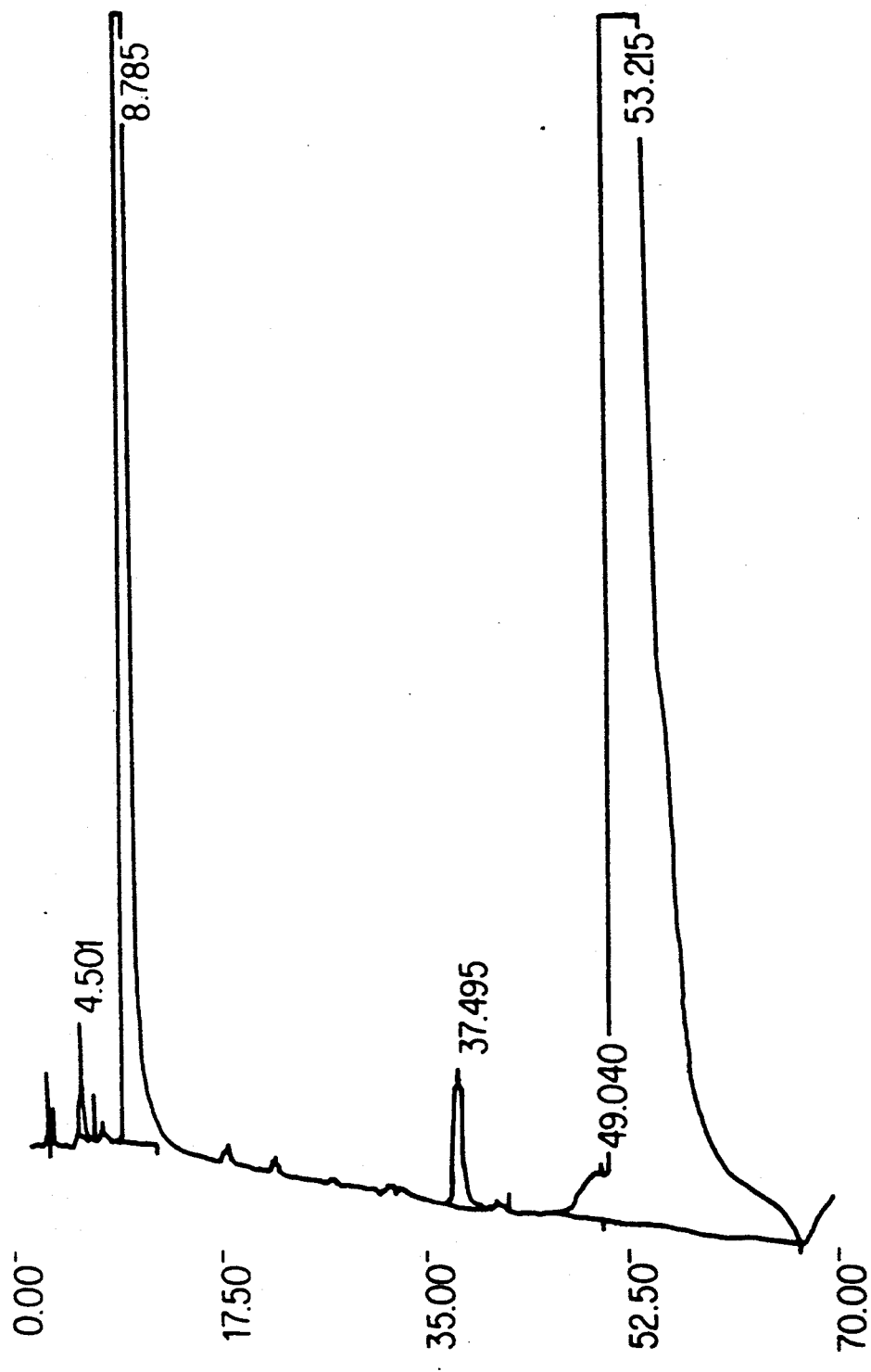
FIG. 2 shows the HPLC chart for FITC-I in the presence of ammonium acetate obtained immediately after heating.
Figure 3:
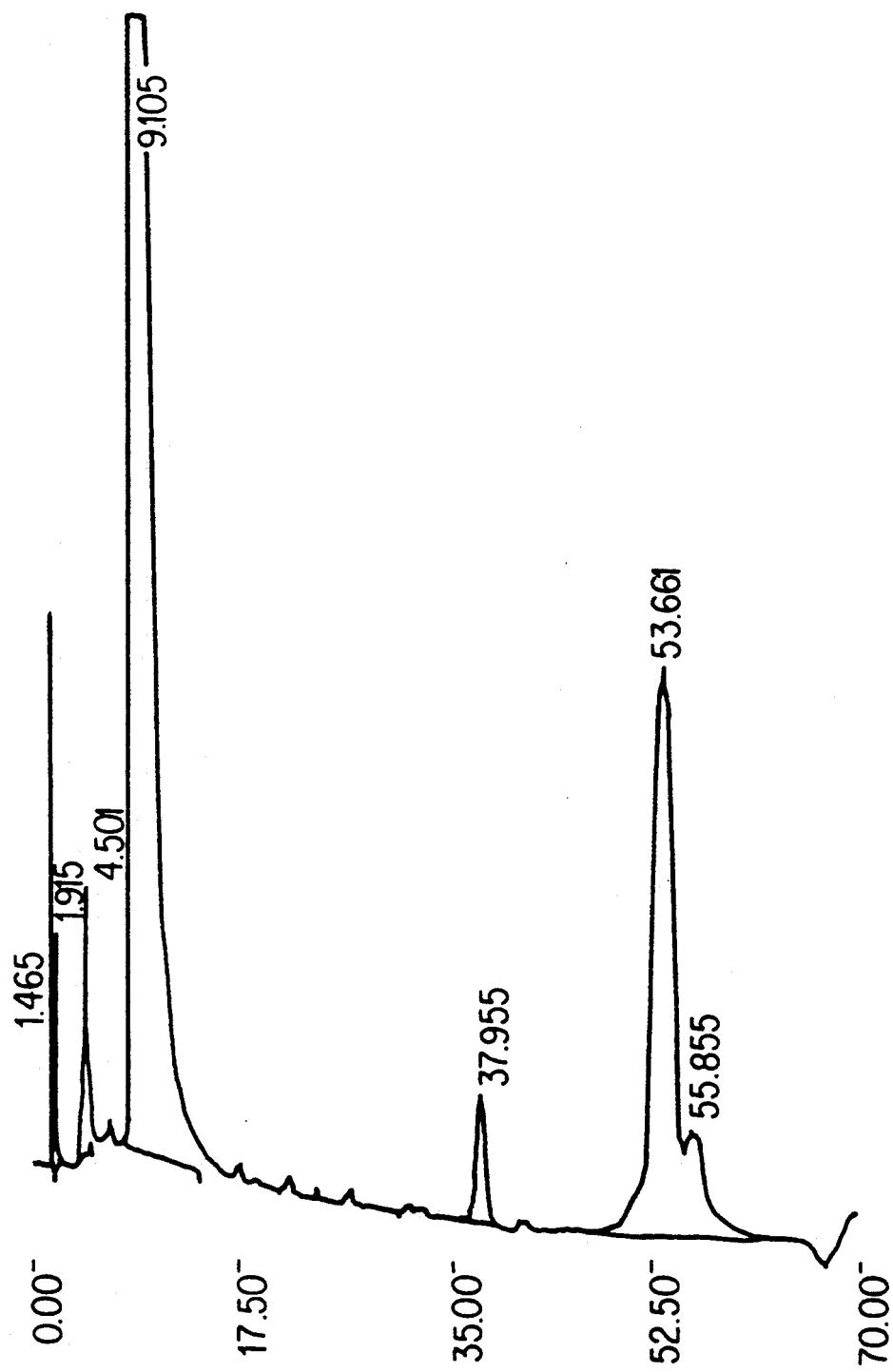
FIG. 3 shows the HPLC chart for FITC-I in the presence of ammonium acetate obtained 5 minutes after heating.
Figure 4:
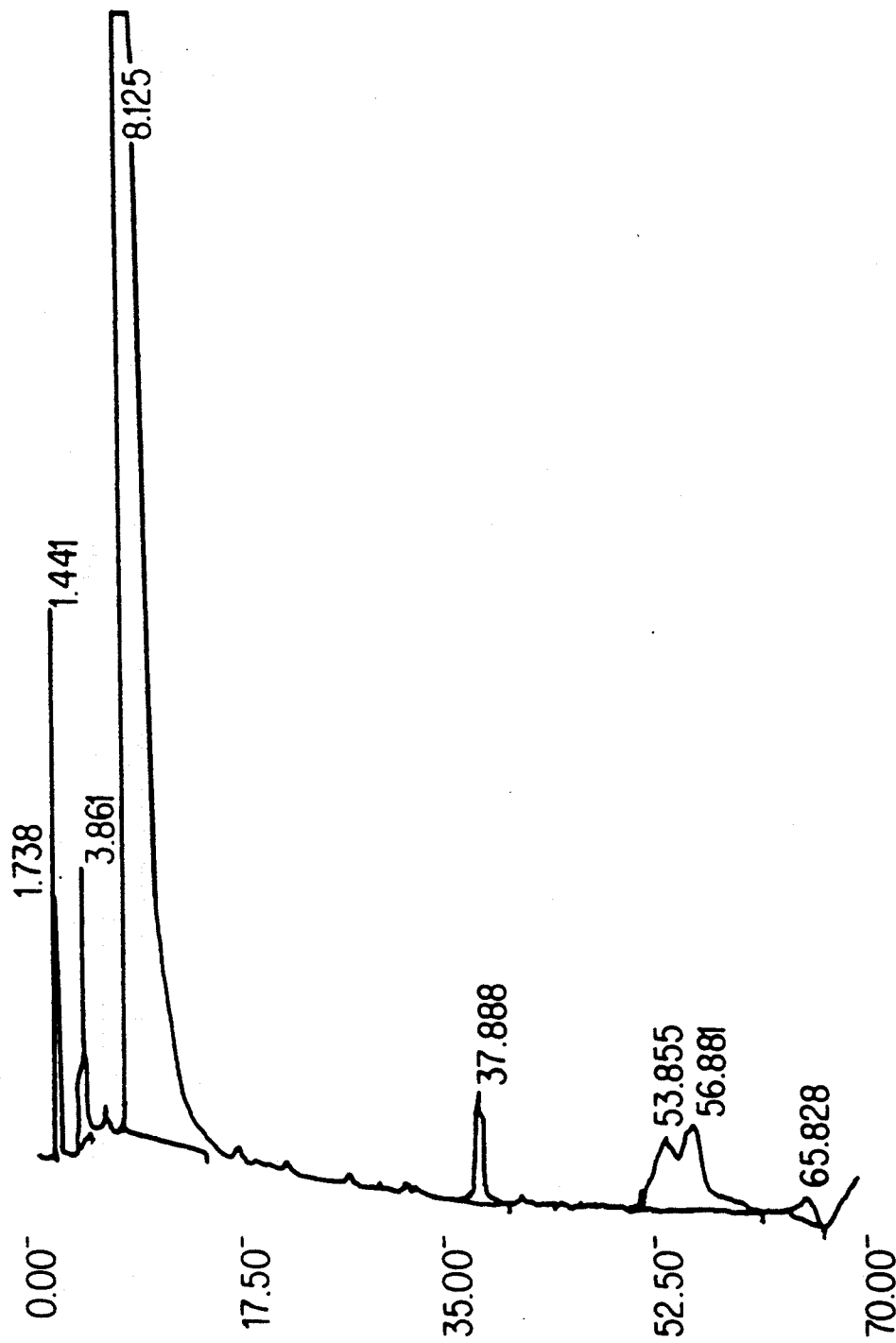
FIG. 4 shows the HPLC chart for FITC-I in the presence of ammonium acetate obtained 10 minutes after heating.

The HPLC chart for FITC-I alone in the absence of ammonium acetate is shown in FIG. 1. The HPLC charts for FITC-I in the presence of ammonium acetate obtained immediately after heating, 5 minutes after heating and 10 minutes after heating are shown in FIGS. 2, 3 and 4, respectively. FITC turned to aminofluorescein by about 90% after 5 minutes, and almost all turned to aminofluorescein after 10 minutes.

EXAMPLE 2

After adding fluoresceinthiohydantoin (FTH)-amino acid (2 pmol), the sample was subjected to HPLC in the same manner as in Example 1.

Figure 5:
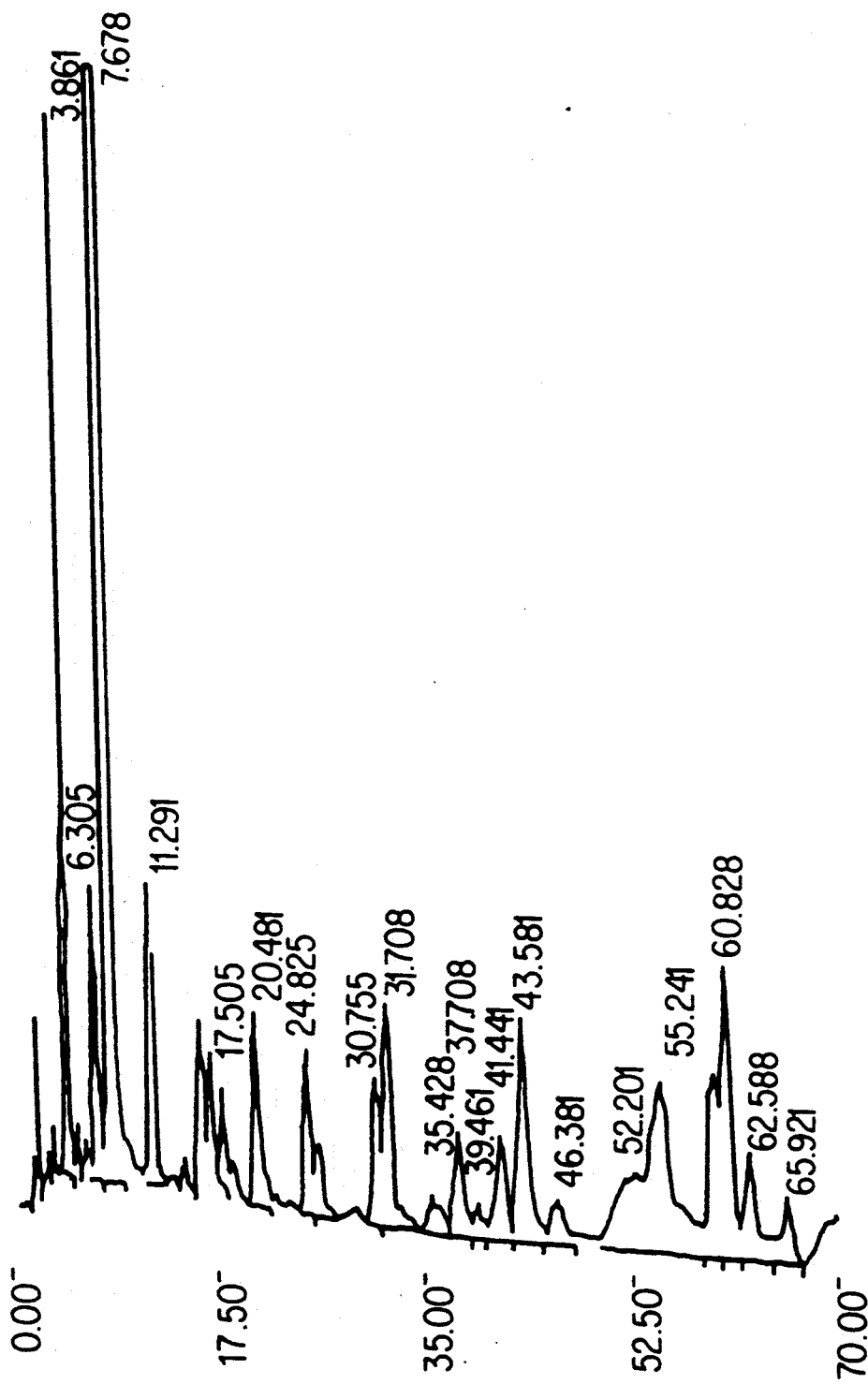
FIG. 5 shows the HPLC chart for FTH-amino acid alone.
Figure 6:
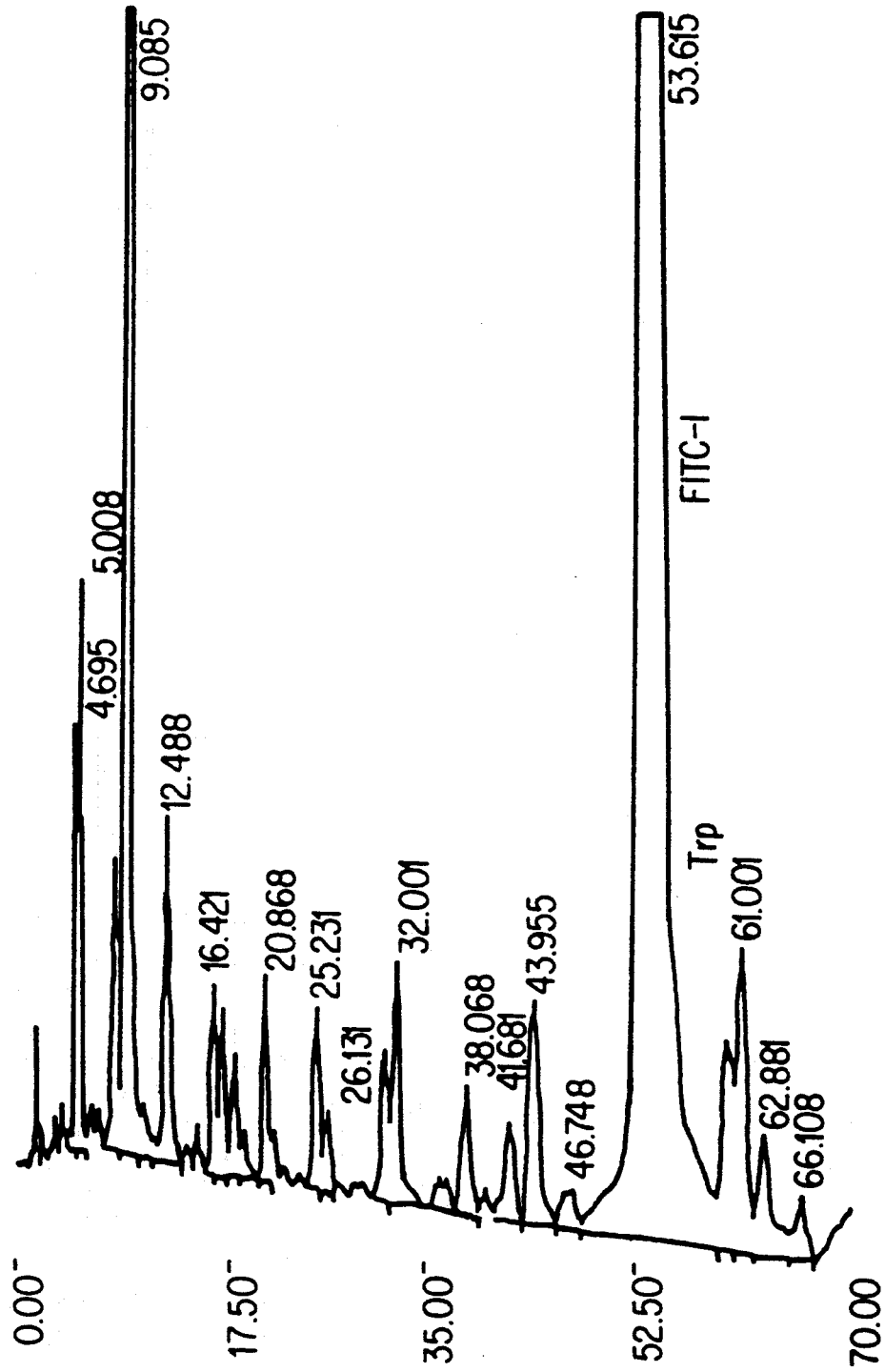
FIG. 6 shows the HPLC chart for FTH-amino acid in the presence of FITC-I obtained immediately after heating according to the method of the present invention.
Figure 7:
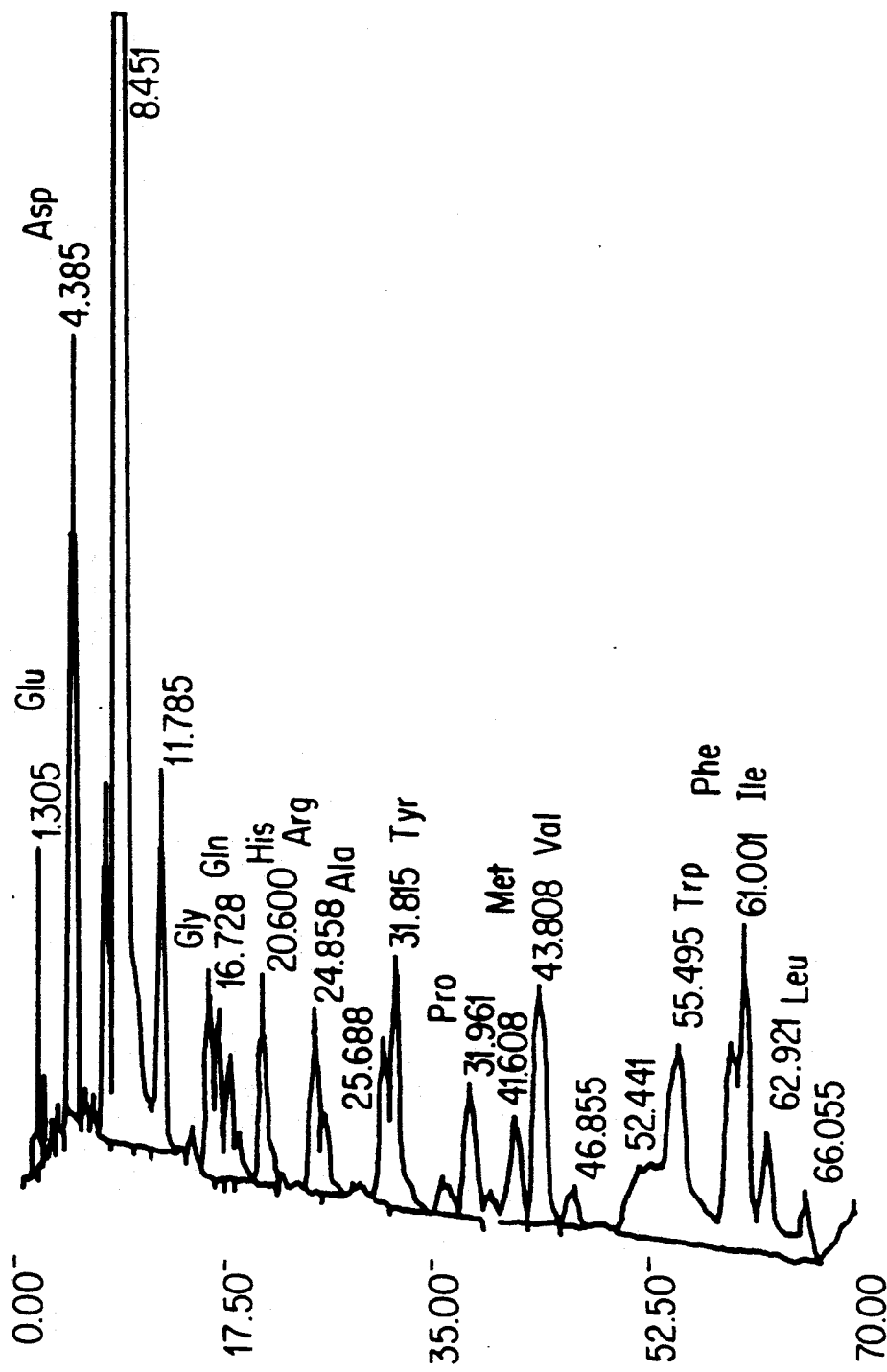
FIG. 7 shows the HPLC chart for FTH-amino acid in the presence of FITC-I obtained 5 minutes after heating according to the method of the present invention.

The HPLC chart for FTH-amino acid alone is shown in FIG. 5. The HPLC charts obtained using FTH-amino acid in the presence of FITC-I according to the method of the present invention immediately after heating and 5 minutes after heating are shown in FIGS. 6 and 7, respectively. FIG. 6 demonstrates that the presence of excess FITC hampers the detection of tryptophan, and FIG. 7 demonstrates that aminofluorescein is eluted near glutamic acid but their peaks do not overlap.

It is therefore desirable to take an initial time of 10 minutes after introducing acetonitrile-ammonium acetate (pH 9.0) in the conversion program when a protein sequencer is used.

What is claimed is:

1. A method for analyzing an amino acid sequence comprising the steps of:
   i) reacting a peptide dissolved in solution with a fluorescent reagent,
   ii) quenching the unreacted fluorescent reagent with an ammonium salt, and
   iii) analyzing the fluorescence spectra of a solution containing the reaction product of the peptide and fluorescent reagent.

2. A method for analyzing an amino acid sequence comprising the steps of:
   i) degrading a peptide dissolved in solution with a fluorescent Edman reagent,
   ii) quenching the unreacted fluorescent reagent with an ammonium salt, and
   iii) analyzing the fluorescence spectra of a solution containing the degradation product of the peptide and the fluorescent reagent.

3. The method according to claim 1 or 2, wherein said ammonium salt is an organic ammonium salt.

4. The method according to claim 1 or 2, wherein said ammonium salt is ammonium acetate.

5. The method according to claim 1, wherein said fluorescent reagent is fluorescein isothiocyanate.

6. The method according to claim 2, wherein said fluorescent Edman reagent is fluorescein isothiocyanate.

7. The method according to claim 1 or 2, wherein said quenching step is heated to about 55° C.

8. The method according to claim 1 or 2, wherein the quenching step is conducted for about 10 minutes.

* * * * *